US006796306B2

(12) United States Patent
Martinez

(10) Patent No.: US 6,796,306 B2
(45) Date of Patent: Sep. 28, 2004

(54) RESPIRATORY APPARATUS WITH FLOW LIMITER

(75) Inventor: Patrice Martinez, Le Perray en Yvelines (FR)

(73) Assignee: Intertechnique, Plaisir Cedex (FR)

( * ) Notice: Subject to any disclaimer, the term of this patent is extended or adjusted under 35 U.S.C. 154(b) by 0 days.

(21) Appl. No.: 10/190,605

(22) Filed: Jul. 9, 2002

(65) Prior Publication Data

US 2003/0010340 A1 Jan. 16, 2003

(30) Foreign Application Priority Data

Jul. 10, 2001 (FR) ........................................... 01 09153

(51) Int. Cl.[7] ............................................. A61M 16/00
(52) U.S. Cl. .............................. 128/204.26; 128/204.21
(58) Field of Search ....................... 128/200.24, 204.18, 128/204.19, 204.21–204.23, 204.25, 204.26, 204.27, 204.29, 205.11, 205.23, 205.24, 206.27; 137/1, 3, 93, 111, 114, 505.24

(56) References Cited

U.S. PATENT DOCUMENTS 3,526,239 A 9/1970 Oroza
3,768,466 A * 10/1973 Johnson ................. 128/204.26
3,995,625 A * 12/1976 Needham ............... 128/204.26
4,335,735 A * 6/1982 Cramer et al. ............. 137/81.1
4,436,090 A * 3/1984 Darling ................. 128/204.26
4,648,397 A * 3/1987 Beale ..................... 128/205.11
4,741,332 A * 5/1988 Beaussant .............. 128/201.23
4,856,507 A * 8/1989 Ouillon et al. ......... 128/204.26
5,351,682 A * 10/1994 Foote .................... 128/205.24
5,460,175 A * 10/1995 Foote et al. ........... 128/205.24
5,540,218 A * 7/1996 Jones et al. ............ 128/201.24

FOREIGN PATENT DOCUMENTS

FR 2 781 381 1/2000
GB 1 577 943 10/1980

* cited by examiner

*Primary Examiner*—Henry A Bennett
*Assistant Examiner*—Teena Mitchell

(57) ABSTRACT

A demand regulator with air dilution for regulating the pressure and flow of a respiratory gas comprises an inlet for additional gas and an outlet leading to a respiratory mask, and also dilution means. Control means switch a supply of pressurized additional gas between at least two passages. At least one of these passages corresponds to an economy flow and has a restricted cross section for limiting the flow of additional gas transmitted to the inlet. The other passage has a cross section which is such that the additional gas has a maximum flow in order to supply the user with additional gas in a physiologically sufficient manner.

11 Claims, 3 Drawing Sheets

FIG.3.
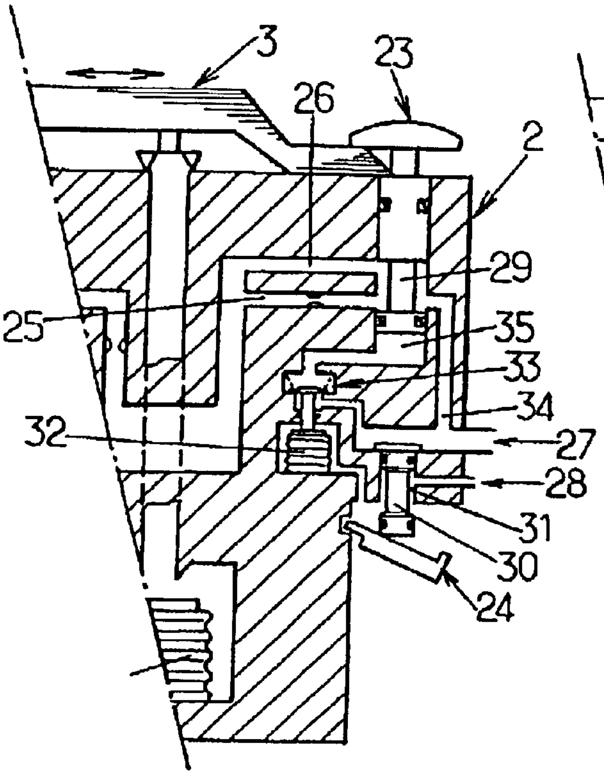
FIG.4.
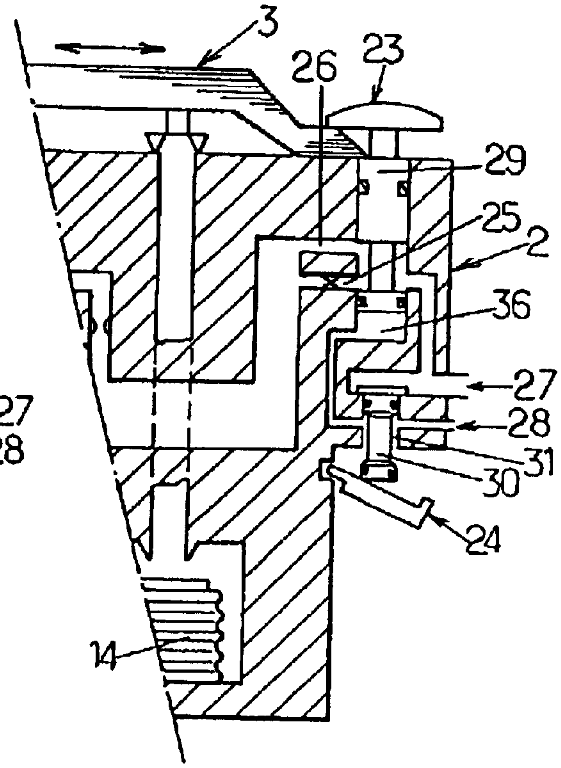
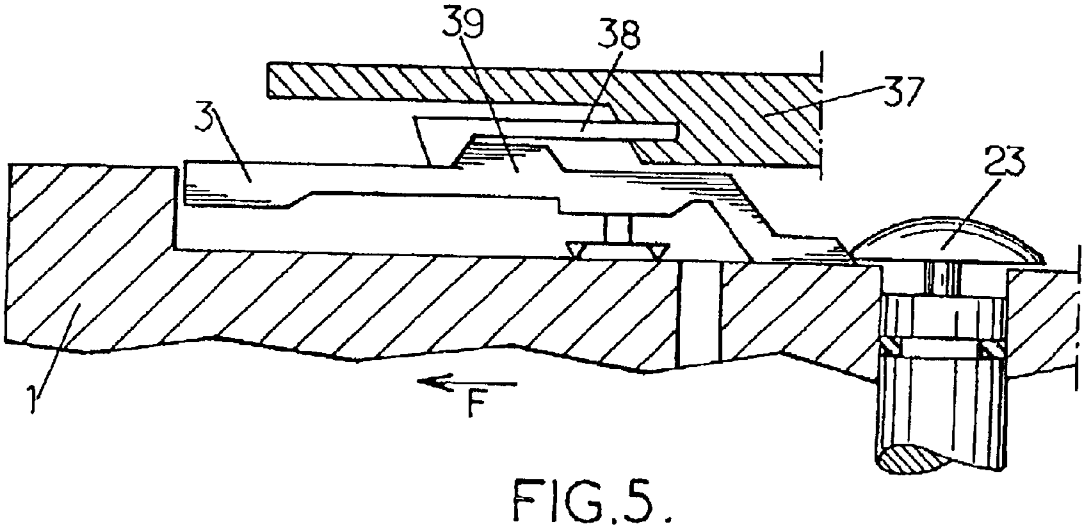
FIG.5.

RESPIRATORY APPARATUS WITH FLOW LIMITER

BACKGROUND OF THE INVENTION

The invention concerns the respiratory apparatuses which are intended to protect persons on board an aircraft, in particular the technical flight crew, from the effects of depressurization at high altitude and/or from fumes or toxic gases.

More precisely, the invention concerns the respiratory apparatuses with a demand regulator with air dilution and the regulators for regulating the pressure and flow of respiratory gas.

A regulator for regulating the pressure and flow of respiratory gas generally comprises, connected to a nose-and-mouth mask:

inlet means for additional gas, generally oxygen, or highly oxygen-enriched air, and an ejector for mixing dilution air with the additional gas and connected to an outlet supplying a user with diluted additional gas.

These respiratory apparatuses are supplied, at the inlet level, with additional gas delivered by pressurized oxygen cylinders, chemical generators, or generators by selective absorption and return of oxygen called OBOGS (acronym for On-Board Oxygen Generator System).

The regulators deliver a respiratory gas for which the course of the enrichment for a given flow as a function of altitude presents an inverse bell shape, that is to say the run of the solid-line curve in FIG. 1. Because of the characteristics of the ejector, the flow of additional gas (oxygen), at low altitude, is much greater than the flow corresponding to the necessary physiological minimum, which for its part increases in a monotonous manner as a function of the cabin altitude (dashed-line curve in FIG. 1).

The flow of additional gas (oxygen) delivered to the respiratory apparatus is too high relative to the requirements and is the cause of excessive consumption of additional gas (oxygen).

An object of the invention is in particular to make available a respiratory apparatus with a regulator for regulating the pressure and flow of respiratory gas, with which it is possible to reduce the flow of additional gas required.

SUMMARY OF THE INVENTION

This object is achieved, by virtue of a regulator of the type described above, additionally comprising, at the inlet of additional gas to the ejector, control means which are able to modify the cross section of passage of the additional gas to the ejector; these means can in particular switch the supply of additional gas between several inlet passages having different cross sections; for example, one of these passages corresponds to a flow called "economy" and has a smaller cross section than that of the other passage called "full flow".

This is because the passage of smaller cross section has a loss of charge which limits the flow of additional gas delivered to the respiratory mask (dotted-line curve in FIG. 1) to a value close to the physiological minimum necessary for a given altitude (dashed-line curve in FIG. 1).

Means are advantageously provided in order to guarantee the safety of the user without intervention on his part or by preventing false manoeuvres.

This object can be achieved in several ways. As an example, a regulator is provided which comprises safety means which have the following characteristics:

they prohibit switching of the supply of additional gas to the passage of smaller cross section when there is no delivery of dilution air (for example upon manual switching to what is called "100%" mode, corresponding to a delivery of pure additional gas to the respiratory mask), and they prohibit the delivery of pure additional gas to the mask by cutting off the air admission, when the supply of additional gas is effected via the passage of smaller cross section.

The regulator according to the invention advantageously comprises the following characteristics in isolation or in combination:

the control means can be actuated manually;

it comprises an altimetric capsule for actuating the control means as a function of the altitude.

When the regulator is fitted on a respiratory mask with inflatable harness, it comprises a harness inflation actuator for bringing the supply of additional gas into communication with the inflatable harness in order to inflate it; the control means advantageously cooperate with the harness inflation actuator in order to switch the supply of additional gas to the "full flow" passage when the harness inflation actuator is used to inflate the harness. For example, the control means switch the supply of additional gas to the "full flow" passage under the effect of the pressure of the gas supplying the harness.

According to another aspect, the invention is a generator of enriched respiratory gas, comprising a pressure regulator according to the invention.

Other aspects, objects and advantages of the invention will become apparent on reading the following detailed description of a number of embodiments.

The invention will also be better understood with the aid of the attached drawings.

BRIEF DESCRIPTION OF THE DRAWINGS

FIG. 3 shows partially and diagrammatically, in cross section, the fluid circuit of another embodiment of the flow regulator shown in FIG. 2;

FIG. 4 shows partially and diagrammatically, in cross section, the fluid circuit of yet another embodiment of the flow regulators shown in FIGS. 2 and 3; and FIG. 5 shows diagrammatically, in cross section, safety means intended for regulators according to the invention.

DETAILED DESCRIPTION OF EMBODIMENTS

Figure 2:
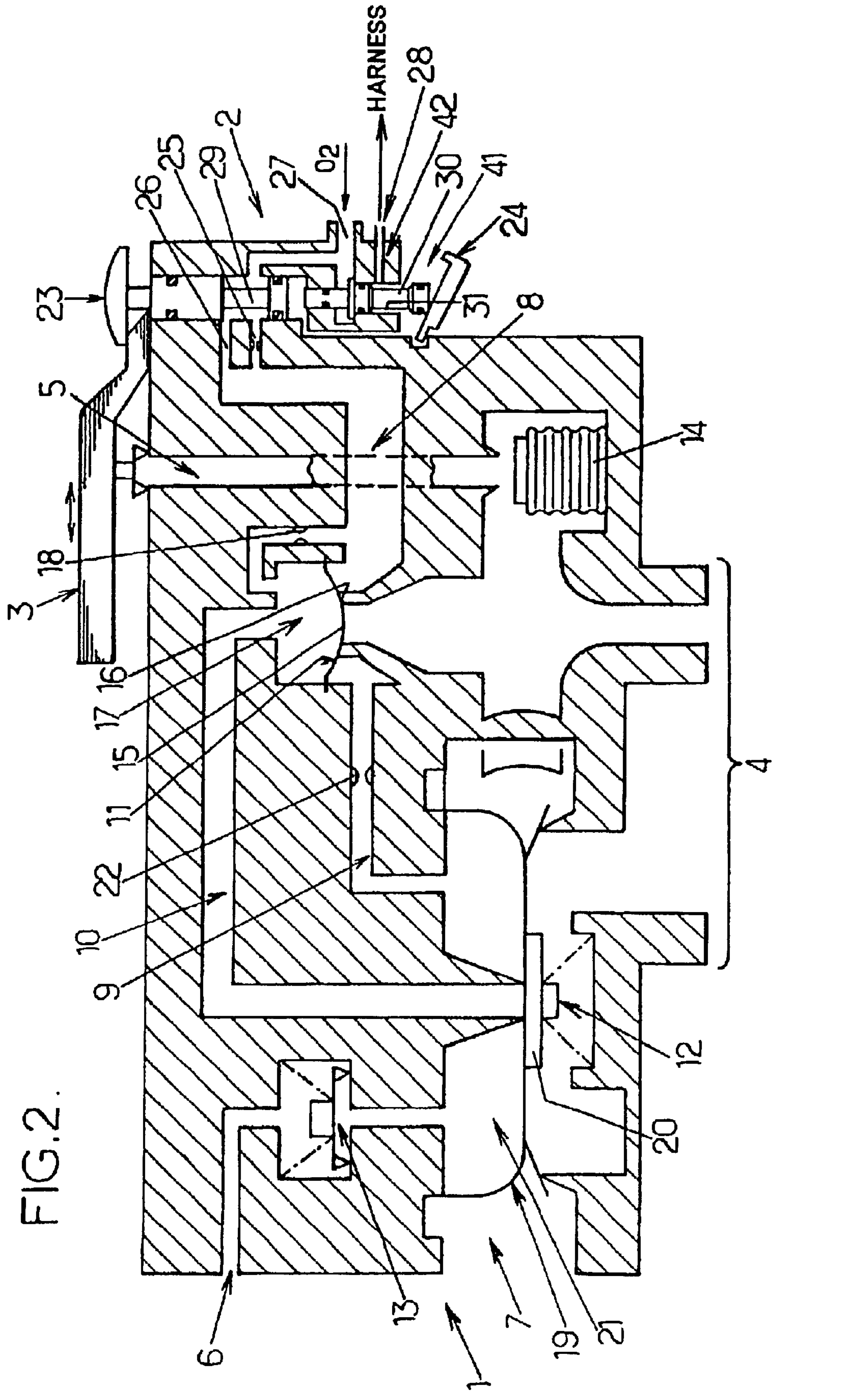
FIG. 2 shows diagrammatically, in cross section, the fluid circuit of one embodiment of a flow regulator according to the invention.

According to a first embodiment, illustrated in FIG. 2, the demand regulator 1 according to the invention is provided with a flow limiter 2 controlled by an actuator for inflating a harness supporting a respiratory mask.

The regulator 1 comprises a housing and a "normal/100%" switch 3, shown in FIG. 2 at position "100%" (air admission closed off).

The housing is made up of several parts joined together and defining a circuit for fluids. It comprises several fluid communications with the outside of the housing: a connector piece 27 for supply of additional gas, a tubing 4 connecting with the inside of a respiratory mask (not shown), a dilution air inlet 5, a passage 6 to the atmosphere, and an exhaled gases outlet 7. It also comprises an inlet 8 in communication with the flow limiter 2.

The housing additionally comprises several internal fluid communications: a primary conduit 9 comprising a calibrated constriction 22, and a secondary conduit 10 connecting compartments separated by a main flap valve 11 to a compartment 21 corresponding to a pilot flap valve 12.

The housing also comprises several switching members for modifying the circulation of the fluids in the circuit defined by the housing. These switching members are the main flap valve 11 and the pilot flap valve 12; the regulator shown has in addition a valve 13 for connecting the compartment 21 of the pilot flap valve 12 to the atmosphere, and an altimetric capsule 14.

The flap valves are of classical configuration. In the case illustrated, the main flap valve 11 is formed by a membrane 15 cooperating with a fixed seat 16. The membrane 15 separates a control chamber 17 from the inlet 8, the primary conduit 9 and the connection tubing 4. The control chamber 17 is connected to the inlet 8 via a calibrated constriction 18. When it is subjected to the inlet pressure of the additional gas, the membrane 15 is pressed against the seat 16, closes the passage of the additional gas in this seat 16 and separates the inlet 8 from the tubing 4.

The pilot flap valve 12 comprises a membrane 19 sensitive to the pressure. The membrane 19 carries an obturator 20 which cooperates with a fixed seat to bring the control chamber 17 into communication with the compartment 21 delimited by the membrane 19, or by contrast to separate the chamber 17 and the compartment 21. The compartment 21 also communicates with the inlet 8 via the constriction 22.

The pilot flap valve 12 also constitutes a release valve permitting escape of the exhaled gases via the outlet 7 for exhaled gases.

The pressure prevailing in the chamber 21 is limited by the venting valve 13 which ensures that the overpressure in the chamber 21 does not exceed a predetermined value.

The altimetric capsule 14 cuts off or authorizes the entry of air via the dilution air inlet 5 as a function of the altitude. At high altitude, the altimetric capsule 14 cuts the entry of dilution air so that the mask is supplied only with the additional gas originating from the flow limiter 2.

The functioning of the regulator 1 is known and is therefore not detailed here. For more details regarding its functioning, reference can be made to the documents FR-A-1 557 809 and FR-A-2 781 381.

The flow limiter 2 comprises a "full flow"/"economy" actuator 23, a passage of restricted cross section 25 and a "full flow" passage 26. The regulator 1 shown has in addition a harness inflation actuator 41, a harness connector 28, a plunger 29 and a piston 30. The harness inflation actuator 41 comprises a tap 42 and a bracket 24.

The "full flow" passage 26 has a cross section which is such that the additional gas is transmitted through this passage with a maximum flow, making it possible to supply the user with pure additional gas physiologically sufficient for the maximum altitude set. The passage of restricted cross section 25 corresponds to an "economy" flow and reduces the flow of additional gas transmitted from the supply 27 to the inlet 8.

The plunger 29 comprises a zone of reduced diameter. Depending on the position of the plunger 29, this zone brings the supply 27 into communication at one and the same time with the passage of reduced cross section 25 and the "full flow" passage 26, or brings the supply 27 into communication only with the passage of reduced cross section 25.

The plunger is displaceable between these two positions by manual action on the "full flow"/"economy" actuator 23 or by a piston 30 belonging to the harness inflation tap 42.

The piston 30 can be brought temporarily into the position illustrated, by virtue of the harness inflation bracket 24. In this rest position, the supply 27 and the harness inflation connector 28 do not communicate. In the other position, a groove 31 of the piston 30 brings the supply 27 and the harness connector 28 into communication.

When the piston 30 is brought into the harness inflation position, it displaces the plunger 29 into its position where the supply 27 is in communication with the passage of restricted cross section 25 and with the "full flow" passage 26, if the plunger 29 is not already in this position. This constitutes a safety measure. Thus, with the embodiment of the invention described here, the user's first inhalation through the mask cannot be limited by an insufficient flow of additional gas. The user, if he so wishes and if he deems it useful, can then change to "economy" mode by bringing the plunger 29 into the "economy" position where only the passage of restricted cross section 25 is in communication with the supply 27. However, also as a safety measure, in order to change to this "economy" mode, the user will first have to position the normal/100% actuator 3 in the "normal" position (position offset towards the left in relation to that shown in FIG. 2), that is to say with intake of dilution air. This is because the passage of restricted cross section 25 does not allow the user to be supplied with 100% additional gas with sufficient flow.

Figure 1:
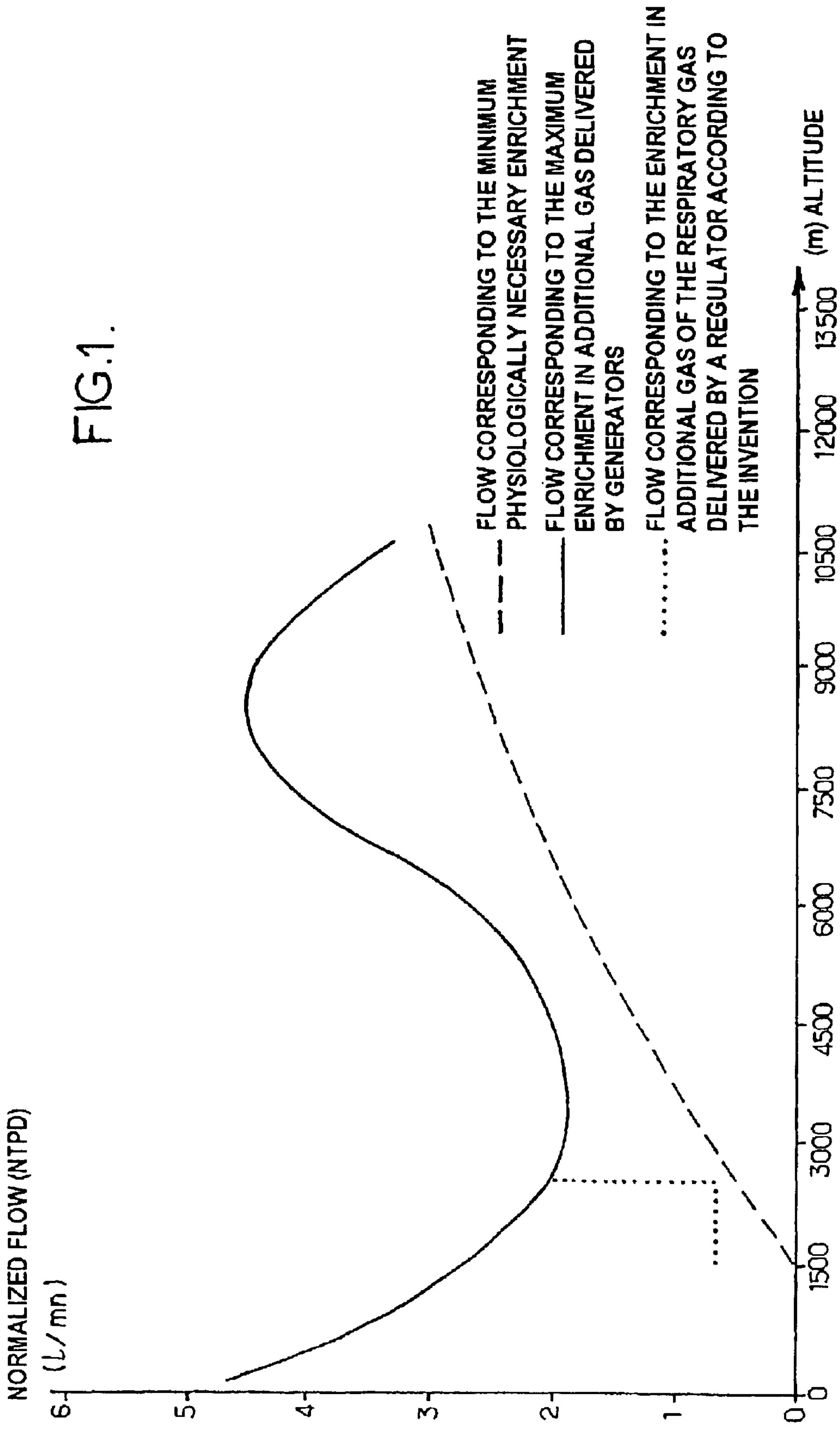
FIG. 1 shows, as a function of altitude, the course of the enrichment in additional gas corresponding to the necessary physiological minimum, the course of the enrichment in additional gas delivered by generators of additional gas, and the flow of additional gas delivered by a flow regulator according to the invention.

FIG. 1 shows a case where the user switches the actuator 23 at 2500 m to limit the flow of additional gas to 0.65 1/min (NTPD) below this altitude (see dotted-line curve). Above this altitude, the user will remain or will return to "full flow" of additional gas by positioning the "full flow"/"economy" actuator 23 in its position permitting communication of the supply 27 with the "full flow" passage 26.

According to yet another variant, the flow limiter 2 comprises several passages of restricted cross section 25 which have different calibres and which can be brought into communication selectively with the supply 27 in such a way as to approach the flow curve corresponding to the physiological minimum by stages corresponding to limited flows.

According to a second embodiment, illustrated in FIG. 3, the demand regulator 1 according to the invention is provided with a flow limiter 2 controlled by altimetric capsule.

The regulator 1 is identical to that described before.

The flow limiter 2, according to this embodiment, comprises an altimetric capsule 32 and an obturator 33 in addition to the "full flow"/"economy" actuator 23, the harness inflation bracket 24, the passage of restricted cross section 25, the "full flow" passage 26, the supply 27 of additional gas, the harness connector 28, the plunger 29 and the piston 30 which have already been described.

However, in this flow limiter 2, the plunger 29 and the piston 30 are independent. The piston 30 is displaced by virtue of the harness inflation bracket 24 in order to bring the groove 31 into communication with the supply 27 and the harness connector 28, but in this displacement the plunger 29 is not stressed, irrespective of its position.

The supply 27 is connected to the passage of reduced cross section 25 and to the "full flow" passage 26 by way of a direct conduit 34. The direct conduit 34 permanently places the supply 27 with the passage of restricted cross section 25. A control conduit 35 makes it possible to transmit the pressure of the additional gas in the supply 27 to the plunger 29.

At low altitude, the obturator 33 is pressed, by a spring or the elasticity of the capsule, onto a seat and closes the control conduit 35. At a predetermined altitude, the altimetric capsule 32 sufficiently stresses the obturator 33 in order to overcome the action of the spring. The control conduit 35 opens and the plunger 29 is displaced under the pressure of the respiratory gas to the "full flow" position, if it was in the "economy" position. Thus, the user is assured of always having a sufficient delivery of respiratory gas irrespective of the altitude.

According to a third embodiment, illustrated in FIG. 4, the demand regulator 1 according to the invention is provided with a flow limiter 2 sensitive to the pressure in the harness.

The regulator 1, in this embodiment, is also identical to that described in relation to the first embodiment.

The flow limiter 2, according to this embodiment, comprises a safety conduit 36 between the piston 30 and the plunger 29, in addition to the "full flow"/"economy" actuator 23, the harness inflation actuator 24, the passage of restricted cross section 25, the "full flow" passage 26, the supply 27 of respiratory gas, the harness connector 28, the plunger 29 and the piston 30 which have already been described.

However, in the same way as in the second embodiment, in this flow limiter 2, the plunger 29 and the piston 30 are independent. The piston 30 is displaced by virtue of the harness inflation bracket 24 in order to bring the groove 31 into communication with the supply 27 and the harness connector 28. In this displacement the plunger 29 is not sent, but the additional gas sent into the harness is also stressed in the safety conduit 36 and with the same pressure. This pressure is sufficient to displace the plunger 29 to the "full flow" position, if it was in the "economy" position. The user's first inhalation through the mask cannot therefore be limited by an insufficient flow of additional gas. In this case too, the user, if he so wishes and if he deems it useful, can then change to "economy" mode by acting on the "full flow"/"economy" actuator 23 to displace the plunger 29 to the "economy" position where only the passage of restricted cross section 25 is in communication with the supply 27, with the same safety measure, assured by the normal/100% actuator 3, as that described in relation to the first embodiment.

Although the regulator 1 can be placed on a user's seat, in civil aircraft it is generally carried on this user's mask. The mask is in standby position or stored in a receiving box 37. In this case, illustrated in FIG. 5, the regulator 1 is advantageously provided with safety means intended to bring the normal/100% actuator 3 to the 100% position when the mask equipped with the regulator 1 is removed from the receiving box 37. These safety means consist for example of an elastic lock 38 placed on the receiving box 37 and intended to cooperate with a stub 39 of the normal/100% actuator 3. When the mask equipped with the regulator 1 is introduced into the receiving box 37, in the direction of the arrow F, the lock 38 brings the normal/100% actuator 3 towards the right in FIG. 5 in such a way that it is necessarily in the 100% position once the mask has been removed from its receiving box 37. As has been explained above, this additionally ensures that the "full flow"/"economy" actuator 23 is not in the "economy" position when the mask is removed from its receiving box 37.

Numerous variants of the invention can be imagined without departing from the scope of the invention. This is the case in particular when several characteristics described above are combined, such as those intended to ensure the safety of the person using the regulator and flow limiter according to the invention.

I claim:

1. Demand regulator with air dilution for regulating the pressure and flow of a respiratory gas, the regulator comprising:

inlet means for additional gas, an ejector for mixing dilution air with the additional gas and connected to an outlet supplying a user with diluted additional gas, in which control means, situated at the inlet, are able to modify the cross section of passage of the additional gas to the ejector by switching a supply of additional gas between several inlet passages, at least two inlet passages having different cross sections.

2. Regulator according to claim 1, comprising an altimetric capsule for actuating the control means as a function of the altitude.

3. Demand regulator with air dilution for regulating the pressure and flow rate of a respiratory gas, the regulator comprising:

inlet means for additional gas, an ejector for mixing dilution air with the additional gas and connected to an outlet supplying a user with diluted additional gas, in which control means, situated at the inlet, are able to modify the cross section of passage of the additional gas to the ejector by switching a supply of additional gas between two inlet passages, one of which has a smaller cross section than the other.

4. Regulator according to claim 3, comprising safety means which prohibit switching of the supply of additional gas to the passage of smaller cross section when there is no delivery of dilution air.

5. Regulator according to claim 3, comprising safety means which prohibit the delivery of pure additional gas to the mask by cutting off the admission of air, when the supply of additional gas is effected via the passage of smaller cross section.

6. Regulator according to claim 3, in which the control means can be actuated manually.

7. Respiratory mask comprising a demand regulator with air dilution for regulating the pressure and flow of a respiratory gas, the regulator comprising:

inlet means for additional gas, an ejector for mixing dilution air with the additional gas and connected to an outlet supplying a user with diluted additional gas, in which control means, situated at the inlet, are able to modify the cross section of passage of the additional gas to the ejector by switching a supply of additional gas between two inlet passages, one of which has a smaller cross section than the other.

8. Mask according to claim 7, comprising a harness inflation actuator for bringing the supply of additional gas into communication with an inflatable harness in order to inflate it.

9. Mask according to claim 8, in which the control means cooperate with the harness inflation actuator in order to switch the supply of additional gas from the passage of smaller cross section to the passage of greater cross section, when the harness inflation actuator is used to inflate the harness.

10. Mask according to claim 8, in which the control means switch the supply of respiratory gas from the passage of smaller cross section to the passage of greater cross section under the effect of the pressure of the gas supplying the inflation of the harness.

11. Generator of enriched respiratory gas, comprising a demand regulator with air dilution for regulating the pressure and flow of a respiratory gas, the regulator comprising:

inlet means for additional gas, an ejector for mixing the dilution air with the additional gas and connected to an outlet supplying a user with diluted additional gas, in which control means, situated at the inlet, are able to modify the cross section of passage of the additional gas to the ejector by switching a supply of additional gas between two inlet passages, one of which has a smaller cross section than the other.

* * * * *